US00PP18324P2

(12) United States Plant Patent
Egger

(10) Patent No.: US PP18,324 P2
(45) Date of Patent: Dec. 18, 2007

(54) ***HEUCHERA* PLANT NAMED 'CINNABAR SILVER'**

(50) Latin Name: ***Heuchera* hybrid**
Varietal Denomination: Cinnabar Silver

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 23 days.

(21) Appl. No.: 11/474,026

(22) Filed: Jun. 23, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—June Hwu
(74) *Attorney, Agent, or Firm*—Klarquist Sparkman, LLP

(57) ABSTRACT

A new and distinct hybrid of *Heuchera* plant characterized by medium sized, dark leaves with heavy silver veiling; brick red colored flowers; compact, mounding habit; excellent vigor.

1 Drawing Sheet

Botanical denomination: *Heuchera* hybrid.
Variety designation: 'Cinnabar Silver'.

The present invention relates to a new and distinct cultivar of *Heuchera* hybrid and given the cultivar name of 'Cinnabar Silver'. *Heuchera* is in the family Saxifragaceae. *Heuchera* 'Cinnabar Silver' originated from a cross between *Heuchera* 45-1 (an unpatented, proprietary plant) as the seed parent, and *Heuchera* 68-2 (an unpatented, proprietary plant) as the pollen parent. Given its ornamental foliage and flower, it is probable that *Heuchera sanguinea* and *H. americana* are in its parentage.

This new *Heuchera* is distinguished by:

1. Medium sized, dark leaves with heavy silver veiling.
2. Brick red colored flowers.
3. Compact, mounding habit.
4. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a three-year-old plant of *Heuchera* 'Cinnabar Silver' growing in a two gallon container in the shade house in April in Canby, Oreg.

FIG. 2 shows the same plant the year before grown under higher light conditions.

DETAILED PLANT DESCRIPTION

The following is a detailed description of the new *Heuchera* cultivar based on observations taken in May of a three-year-old specimen grown a three gallon container in an open air shade house with 50% shade cover and added irrigation in the summer months in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Botanical classification: *Heuchera* hybrid.
Variety denomination: 'Cinnabar Silver'.
Parentage: *Heuchera* 45-1 (seed parent)×*Heuchera* 68-1 (pollen parent).

Plant:
- *Form.*—Basal rosette, herbaceous perennial.
- *Hardiness.*—USDA Zone 4 to 9.
- *Size.*—22 cm tall from the ground to the top of the foliage and 40 cm wide.
- *Habit.*—Mounding.
- *Vigor.*—Excellent.
- *Roots.*—Fibrous, freely branching, fine, and white in color. Roots develop easily from cuttings.

Leaf:
- *Type.*—Simple.
- *Arrangement.*—Rosette.
- *Shape.*—Broadly ovate, flattened appearance.
- *Lobing/division.*—5 to 7 shallow lobes.
- *Venation.*—Palmate.
- *Margins.*—Crenate.
- *Apex.*—Obtuse.
- *Base.*—Cordate, lobes sometimes slightly overlapping at the base.
- *Blade size.*—8.5 to 10 cm long and 8.5 to 9 cm wide.
- *Surface texture.*—Sparsely glandular on both sides, satiny in appearance, leathery feeling.
- *Petiole size.*—10 cm long and 2 to 3 mm wide.
- *Petiole surface texture.*—Glandular-pubescent.
- *Petiole color.*—Brown 200D.
- *Leaf color.*—Spring, summer topside — Before flowering the new leaves are deep purple, Greyed Purple 187A with a purple silver veil, Violet 87C. Once the flowers open the leaf color is silver, Grey Green 198D with veins Grayed Purple 187A. Bottom side all seasons — Between Grayed Purple 187A and Red Purple 59A and shiny. Winter topside — Silver, Greyed Green 198D with veins between Yellow Green 147A and Brown 200A.

Inflorescence:

*Type.*—Thyrse.

*Number of flowers.*—150 per thyrse.

*Number of thyrse in spring.*—30 in first flush.

*Peduncle.*—With 0 to 3 petiolate cauline leaves, ovate, blades grow to 3 cm long and 3 cm wide, margin crenate, base usually cordate. Height — 46 cm. Diameter — 0.5 cm near base. Color — Greyed Purple 187A. Surface texture — Glandular hairs.

*Pedicel.*—Length — Variable. Surface texture — Glandular hairs. Color — Grayed Purple 187A.

*Bloom period.*—May in Canby, Oreg.

Flower bud:

*Size.*—2 mm wide and 4 mm long.

*Description.*—Glandular puberulent, ovoid.

*Color.*—Pink, Greyed Purple 185D at base and Greyed Yellow 160C at tip.

Flower:

*Type.*—Perfect, zygomorphic.

*Shape.*—Campanulate.

*Size.*—7 mm long and 7 mm wide.

*Petal description.*—5 in number, reflexed, 3 mm long and 0.8 mm wide, glandular on backs, margins mostly entire, tip acute, base attenuate, bright pink, Red 52B.

*Calyx description.*—7 mm deep and 7 mm wide, 5 lobes, ovate, cut ¼ way to the base, with glandular hairs, reflex, tip acute, margins entire, inside color is between Greyed Red 179A and Red 47A, outside base is Greyed Red 178A, middle and lobes are Greyed Red 179A.

*Stamen description.*—5, reduced, filaments White 155A, 2 mm long, anthers sterile, Greyed Yellow 161C.

*Pistil.*—6 mm long, Yellow Green 154C, two beaked.

*Fragrance.*—None.

*Lastingness.*—Each thyrse blooms for about 2 weeks on the plant.

Fruit:

*Type.*—Two-beaked ovoid capsule.

*Color.*—Brown 200D.

Seed:

*Shape.*—Linear.

*Size.*—2 mm. long.

*Color.*—Black. RHS 202A.

Pest and disease tolerance: Excellent disease resistance to powdery mildew, the common problem of *Heuchera*. Susceptible to *Heuchera* rust and root weevils.

COMPARISON TO SIMILAR *HEUCHERAS*

Compared to *Heuchera* 'Swirling Fantasy' (U.S. Plant Pat. No. 14,542), *Heuchera* 'Cinnabar Silver' has brick red colored flowers rather than pinkish red. The new cultivar has shorter flower stalks and much more leaf silvering.

Compared to *Heuchera* 'Cherries Jubilee' (U.S. Plant Pat. No. 11,377), the new variety has larger, darker flowers and darker, heavily veiled leaves.

Compared to the seed parent, *Heuchera* 45-1 (an unpatented, proprietary plant), the new variety has shorter flowering stems and larger flowers of brick red rather than dull red.

Compared to the pollen parent, *Heuchera* 68-2 (an unpatented, proprietary plant), the new variety has darker leaves, a heavier veil, and brick red rather than dull orange red flowers.

I claim:

1. A new and distinct hybrid of *Heuchera* plant as herein illustrated and described.

* * * * *

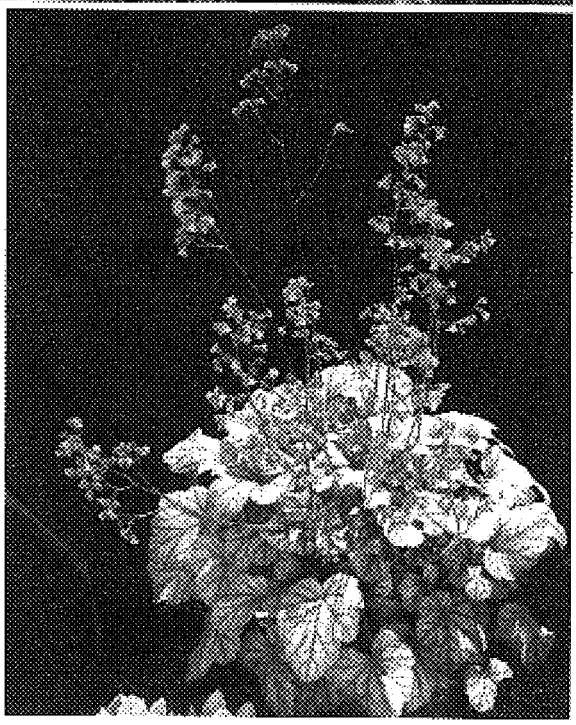

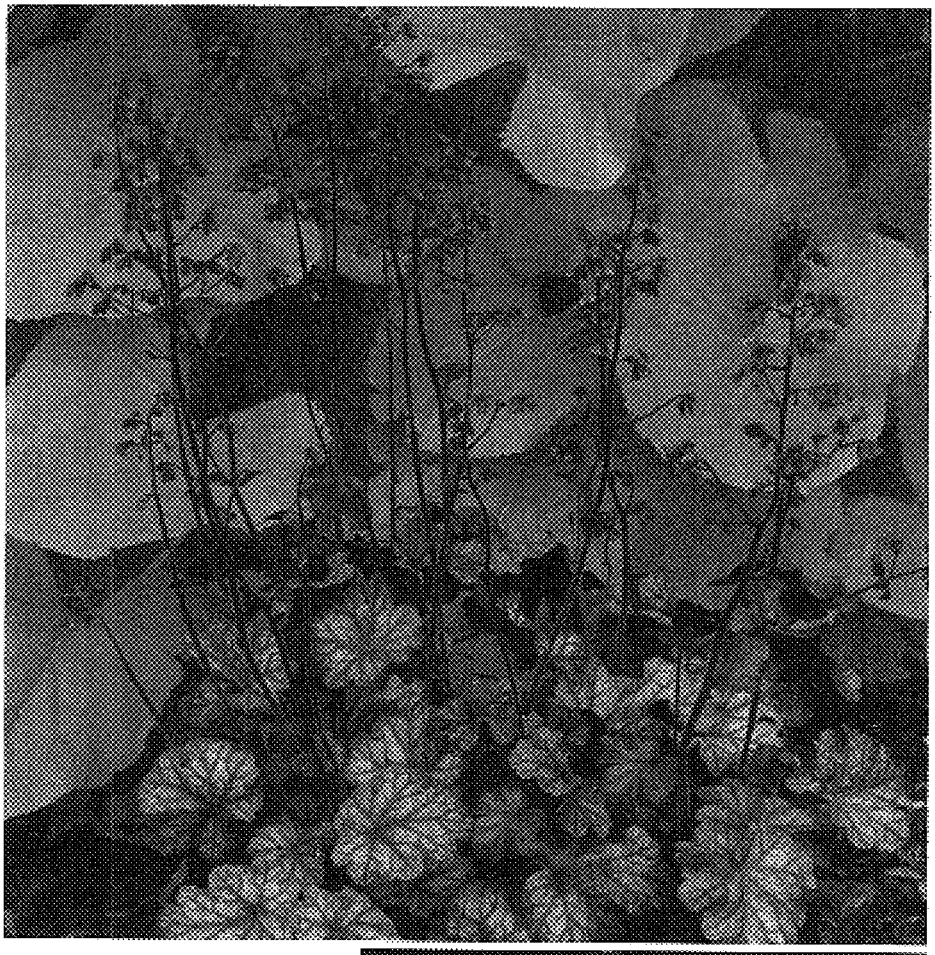
*Figure 1 above*
*Figure 2:*